United States Patent [19]

Beck et al.

[11] Patent Number: 5,008,463
[45] Date of Patent: Apr. 16, 1991

[54] PROCESS FOR THE PREPARATION OF FORMALDEHYDE

[75] Inventors: Horst-Philipp Beck, Dudweiler/Saar; Gerhard Emig, Erlangen; Günther Wiesgickl, Grosswallstadt; Karlheinz Burg; Karl-Friedrich Mück, both of Wiesbaden, all of Fed. Rep. of Germany

[73] Assignee: Hoechst Aktiengesellschaft, Frankfurt, Fed. Rep. of Germany

[21] Appl. No.: 541,629

[22] Filed: Jun. 21, 1990

[30] Foreign Application Priority Data

Jun. 24, 1989 [DE] Fed. Rep. of Germany ....... 3920811

[51] Int. Cl.$^5$ .................. C07C 45/00; C07C 47/04
[52] U.S. Cl. ................................ 568/487; 568/449
[58] Field of Search ................................ 568/487, 449

[56] References Cited

U.S. PATENT DOCUMENTS 4,181,629  1/1980  Cairati et al. ..................... 568/487
4,788,347 11/1988  Sagou et al. ....................... 568/487

FOREIGN PATENT DOCUMENTS 0495925   9/1953  Canada .............................. 568/487
0890659   5/1971  Canada .............................. 568/487
3719055  12/1988  Fed. Rep. of Germany .
0019251   6/1972  Japan ................................ 568/487
60-089441 10/1983  Japan ................................ 568/487
433782    3/1976  U.S.S.R. ........................... 568/487

OTHER PUBLICATIONS

Ullmann 11: 693-694, 4th ed. (1976), pub. Verlag Chemie, Weinheim.

Primary Examiner—Werren B. Lone

[57] ABSTRACT

The process dehydrogenates methanol in the presence of a catalyst based on aluminum oxide, alkali metal aluminate and/or alkaline earth metal aluminate with the exclusion of oxygen at a temperature of 650° to 1050° C. in a reactor whose inner wall is composed entirely or partly of aluminum oxide. The process gives anhydrous formaldehyde which contains only very minor impurities.

9 Claims, No Drawings

PROCESS FOR THE PREPARATION OF FORMALDEHYDE

The present invention relates to a process for the preparation of formaldehyde by dehydrogenating methanol in the presence of a catalyst at elevated temperature.

A plurality of processes have been disclosed for the preparation of formaldehyde from methanol. In the art, it is usual to oxidize methanol to formaldehyde by the following scheme $$CH_3OH + \tfrac{1}{2}O_2 \rightarrow CH_2O + H_2O \qquad (I)$$

this oxidation being carried out on iron oxide- and molybdenum oxide-containing catalysts at 350° to 450° C. It is likewise customary to oxidatively dehydrogenate methanol giving formaldehyde according to the equations $$CH_3OH \rightleftharpoons CH_2O + H_2 \qquad (IIa)$$

$$H_2 + \tfrac{1}{2}O_2 \rightleftharpoons H_2O \qquad (IIb)$$

on silver catalysts at 600° to 720° C. Both processes are described in Ullmanns Encycl. der techn. Chemie, Volume 11, pp. 693-694, 4th edition, 1976, published by Verlag Chemie, Weinheim.

For instance, a process has been disclosed for the preparation of formaldehyde from methanol by dehydrogenation at elevated temperature, in which the reaction is carried out in the presence of a catalyst containing at least one sodium compound at a temperature of 300° C. to 800° C. (DE-A-3,719,055).

Another publication in which the use of a silver oxide-containing catalyst is mentioned, states that it is essential that the impurities $Al_2O_3$ and MgO are absent (JP-A-60/089,441 = Derwent Report 85-156891/26).

However, the known catalysts do not allow an economical preparation of formaldehyde by dehydrogenating methanol. The known processes give yields of formaldehyde which are in every case less than 70% and the conversions, i.e. the ratio of converted methanol to methanol metered in, were never greater than 95%. Consequently, it was desirable to achieve as good or better results using catalysts which are cheaper and easier to prepare.

The present invention accordingly provides a process for the preparation of formaldehyde by dehydrogenating methanol in the presence of a catalyst at elevated temperature., the reaction being carried out at a temperature of 650° to 1050° C. with the exclusion of oxygen in the presence of aluminum oxide, alkali metal aluminate and/or alkaline earth metal aluminate as catalyst in a reactor whose inner wall is composed entirely or partly of aluminum oxide.

The dehydrogenation reaction can be described by the equation $$CH_3OH \rightleftharpoons CH_2O + H_2 \qquad (IIa)$$

Surprisingly, the process gives formaldehyde with a good selectivity and yield.

Examples of suitable aluminum compounds for preparing the catalyst are the oxides, hydroxides, carbonates, bicarbonates, oxalates, acetates or nitrates alone or mixed with corresponding alkali metal or alkaline earth metal compounds.

Suitable cations of the alkali metal and alkaline earth metal compounds are those from main groups 1 and 2 of the periodic table such as lithium, sodium, potassium, rubidium, magnesium, calcium, strontium and barium, preferably however lithium and sodium or mixtures thereof. The catalyst can be used in an industrially customary form, for example in the form of spheres or rods. It can be used directly, i.e. in the initial form of the compounds or first be activated thermally, for example in air and/or chemically. In any case, the starting compounds are converted to the active form at the high temperatures within the reactor. Anionic groups such as carbonate, bicarbonate, oxalate, acetate or nitrate can no longer be detected after treatment at temperatures corresponding to the reaction temperatures.

The reaction temperatures during the dehydrogenation of the methanol are generally 650° to 1050° C., preferably 820° to 950° C. and in particular 850° to 920° C. The pressure prevailing during the process is not crucial. The methanol can be dehydrogenated at reduced pressure, atmospheric pressure or elevated pressure, preferably however at a pressure of about 1.2 bar.

The reactor can, for example, be tubular and is preferably composed of corundum.

The methanol which is present in the reactor in the gaseous state can be reacted as such or as a mixture with carbon dioxide and optionally also with an inert gas, preferably nitrogen. Furthermore, water can also be added to the reaction mixture. The added compounds have a beneficial effect on the long term activity of the catalyst since these substances counteract the deactivation of the catalyst. Generally, up to 1% by weight of water and/or up to 3 mol % of carbon dioxide, each relative to the amount of methanol metered in, are used.

The process according to the invention can be carried out batchwise, or preferably continuously. In continuous operation, 0.1 to 100 kg, preferably 0.5 to 10 kg, of methanol are converted per hour and per kilogram of catalyst.

The quantities quoted in the Examples were calculated as follows:

$$\text{Conversion (in \%)} = \frac{\text{methanol converted (mol)}}{\text{methanol metered in (mol)}} \times 100$$

$$\text{Yield (in \%)} = \frac{\text{formaldehyde formed (mol)}}{\text{methanol metered in (mol)}} \times 100$$

$$\text{Selectivity (in \%)} = \frac{\text{formaldehyde formed (mol)}}{\text{methanol converted (mol)}} \times 100$$

A small amount of carbon monoxide was formed in a side reaction. In carrying out the process in which water was added to the reaction mixture, small amounts of carbon dioxide and methane were detected in the product gas. In no case was it possible to detect water in the product gas, even any of that water which had been metered in.

EXAMPLES

Each of the examples describes the dehydrogenation of methanol in accordance with equation (IIa).

(1) Sodium carbonate and aluminum hydroxyacetate were mixed so that there was one mole of aluminum per mole of sodium. The mechanical mixture was calcinated at 900° C. in air for 3 days. The resulting product was ground and pressed into pellets having a diameter of 6 mm. These were comminuted and a particle size fraction having a diameter of 2 mm ±1 mm was selected therefrom. 1.71 g of the catalyst obtained in this manner having a bulk volume of 2.2 ml were introduced into a tube made from. $Al_2O_3$ having an internal diameter of 12 mm. The methanol which was metered in contained 0.1 percent by weight of water. A reaction temperature of 900° C. and a feed rate of 3.97 mol/h (10 mol % of methanol, the remainder nitrogen ($N_2$)), gave a methanol conversion of 100% and a formaldehyde yield of 69.4%.

(2) Lithium carbonate and aluminum nitrate were mixed so that there was one mole of lithium per mole of aluminum. The mechanical mixture was calcinated in air for 1½ days. The resulting catalyst was pressed into pellets having a diameter of 6 mm. These were comminuted and a particle size fraction having a diameter of 1 mm ±0.5 mm was selected therefrom. 0.75 g of this substance having a bulk volume of 1 ml was added to an $Al_2O_3$ tube having an internal diameter of 12 mm. The methanol metered in contained 0.05 percent by weight of water. A reaction temperature of 850° C. and a feed rate of 3.97 mol/h (10 mol % of methanol, the remainder $N_2$) gave a methanol conversion of 49.2% and a formaldehyde yield of 23.9%.

(3) (Comparison) 1.08 g of $Al_2O_3$ (0.8 ml bulk volume) having a purity of 99.7% was added to a quartz tube having an internal diameter of 12 mm. A reaction temperature of 750° C. and a feed rate of 1.33 mol/h (10 mol % of methanol in $N_2$) gave a methanol conversion of 6.4% with 100% formaldehyde selectivity.

(4) Aluminum nitrate was mixed with potassium oxalate so that there was one mole of potassium per mole of aluminum. The mixture was calcinated in air at 850° C. for 5 days. The resulting product was pressed into pellets having a diameter of 6 mm. These were comminuted and a particle size fraction having a diameter of 3 mm ±1 mm was selected therefrom. 1.14 g of the catalyst obtained in this manner having a bulk volume of 1.5 ml was added to an $Al_2O_3$ tube having an internal diameter of 12 mm. The methanol introduced contained 0.05 percent by weight of water. A reaction temperature of 850° C. and a feed rate of 5.53 mol/h (7.78 mol % of methanol in $N_2$) gave a methanol conversion of 92.7% and a formaldehyde yield of 40%.

(5) 1.14 g of the catalyst produced according to Example 4 having a bulk volume of 1.5 ml was added to an $Al_2O_3$ tube having an internal diameter of 12 mm. The methanol introduced contained 0.05 percent by weight of water. A reaction temperature of 750° C. and a feed rate of 2.76 mol/h (14.4 mol % of methanol, the remainder $N_2$) gave a methanol conversion of 71.7%. The formaldehyde yield was 14.9%.

(6) Lithium carbonate, sodium carbonate and aluminum hydroxyacetate were mixed so that there were one mole of lithium and one mole of sodium per 2 moles of aluminum. The mechanical mixture was heat-treated at 850° C. in air for 2 days. The product is pressed into pellets having a diameter of 6 mm. These were comminuted and a particle size fraction having a diameter of 1 mm ±0.5 mm was selected therefrom. 2.41 g of this fraction having a bulk volume of 2.9 ml were added to an $Al_2O_3$ tube having an internal diameter of 12 mm. The methanol metered in contained 0.05 percent by weight of water. A reaction temperature of 900° C. and a feed rate of 3.97 mol/h (10 mol % of methanol, the remainder $N_2$) gave a methanol conversion of 97.4% and a formaldehyde yield of 72.8%. Even after 120 g of methanol had been converted per g of catalyst, there was no discernible decline in activity.

(7) 0.93 g of the catalyst prepared according to Example 6 having a bulk volume of 1.1 ml was added to an $Al_2O_3$ tube having an internal diameter of 12 mm. A reaction temperature of 750° C. and a feed rate of 4.01 mol/h (10 mol % of methanol, 1 mol percent of $CO_2$, the remainder $N_2$) gave a methanol conversion of 22.4% and a formaldehyde selectivity of 100%.

(8) Example 7 was repeated but the methanol metered in contained 0.05 percent by weight of water. A reaction temperature of 900° C. and a feed rate of 3.97 mol/h (10 mol % of methanol, the remainder gave a methanol conversion of 97.3%. The selectivity was 69.4%.

(9) (Comparative example) The procedure of Example 1 of DE-A-3,719,055 was followed but the throughput of methanol was adapted to Example 1 of the present application. Sodium carbonate was calcinated stepwise in a stream of hydrogen. The heating rate was 5° C./min. At 100° C., 500° C. and 600° C., the temperature was in each case maintained constant for three hours. The final temperature of 700° C. was maintained for five hours. 2 g of the catalyst which had been obtained in this manner were added to a quartz tube having an internal diameter of 10 mm. 0.397 mol per hour of a nitrogen-methanol mixture containing 10% of methanol was passed through the particulate catalyst. At 700° C., the methanol conversion was 22%. The formaldehyde selectivity was 68%. Over the entire time interval, about 1.5 g of formaldehyde was formed per gram of catalyst before the catalyst became completely carbonized (deactivated).

The experiment was repeated at 600° C., the methanol conversion being 18% and the formaldehyde selectivity being 89%.

We claim:

1. A process for the preparation of formaldehyde by dehydrogenating methanol in the presence of a catalyst at elevated temperature, which comprises carrying out the reaction at a temperature of 650° to 1050° C. with the exclusion of oxygen in the presence of at least one of the compounds aluminum oxide, alkali metal aluminate and alkaline earth metal aluminate as catalyst in a reactor whose inner wall is entirely or partly composed of aluminum oxide.

2. The process as claimed in claim 1, wherein the starting material used is methanol alone or a mixture of methanol with an inert gas.

3. The process as claimed in claim 2, wherein the inert gas used is nitrogen.

4. The process as claimed in claim 1, wherein water and/or carbon dioxide is metered into the starting material.

5. The process as claimed in claim 4, wherein up to 1% by weight of water and/or up to 3 mol % of carbon dioxide, relative to the amount of methanol used, is metered in.

6. The process as claimed in claim 1, wherein the reaction is carried out at a temperature of 820° to 950° C.

7. The process as claimed in claim 1, wherein the catalyst used is an alkali metal aluminate which contains lithium and/or sodium as the alkali metal.

8. The process as claimed in claim 1, wherein the reactor used is a tube of corundum.

9. The process as claimed in claim 1, wherein the catalyst used is in the form of approximately spherical particles having diameters in the range of from 1 to 3 mm.

* * * * *